United States Patent [19]

Kaspers et al.

[11] Patent Number: 4,701,454
[45] Date of Patent: Oct. 20, 1987

[54] FUNGICIDAL COMPOSITIONS OF OXADIXYL AND ANILAZINE AND THEIR USE

[75] Inventors: Helmut Kaspers; Jiri Duben, both of Leverkusen, Fed. Rep. of Germany; Ulrich Gisi, Wenslingen, Switzerland

[73] Assignee: Sandoz Ltd., Basel, Switzerland

[21] Appl. No.: 831,392

[22] Filed: Feb. 19, 1986

[30] Foreign Application Priority Data

Feb. 19, 1985 [GB] United Kingdom ................. 8504181

[51] Int. Cl.[4] ...................... A01N 43/66; A01N 43/76
[52] U.S. Cl. ..................................... 514/245; 514/376
[58] Field of Search ......................................... 514/245

[56] References Cited

U.S. PATENT DOCUMENTS 2,720,480 10/1955 Wolf ..................................... 514/245

*Primary Examiner*—Leonard Schenkman
*Assistant Examiner*—Joseph A. Lipovsky
*Attorney, Agent, or Firm*—Gerald D. Sharkin; Richard E. Vila

[57] ABSTRACT

The invention relates to a method of combatting fungal diseases with the aid of
(a) an oomycetes controlling fungicide of formula I

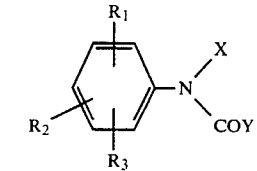

wherein
$R_1$, $R_2$, independently, are H or $CH_3$
$R_3$ is H, Cl, Br,
X is $CH(CH_3)COOCH_3$, 2-oxo-tetrahydrofuran-3-yl, 2-oxo-tetrahydrothien-3-yl or 2-oxo-1,3-oxazolidin-3-yl and
Y is $CH_2OCH_3$, 2-furyl, benzyl, $CH_2Cl$, cyclopropyl or 3-isoxazolyl,
in association with
(b) Anilazine of formula II

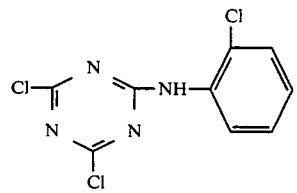

in admixture or separately in a fungicidally effective aggregate amount, and optionally other fungicides, and to fungicidal compositions comprising such fungicides.

6 Claims, No Drawings

FUNGICIDAL COMPOSITIONS OF OXADIXYL AND ANILAZINE AND THEIR USE

The present invention relates to fungicides.

Certain acylated aniline derivatives are known to possess fungicidal activity, in particular against Oomycetes.

Research Disclosure, November 1979, pages 632-3, No. 18745, (hereinafter RD) discloses fungicidal acylated aniline compounds of a general formula embracing i.a. metalaxyl and furalaxyl and states that the fungicidal properties of such compounds can be enhanced or in some cases a broadening of activity spectrum achieved by the addition of further microbicides. RD lists by way of example one hundred and twenty one microbicides, including anilazine, which may be used in admixture with certain acylated anilines and states that in some cases the addition of such microbicides produces a synergistically increased activity. RD does not however specifically disclose an mixture of any acylated aniline with anilazine.

It has now been found that the use of
(a) an oomycetes controlling fungicide of formula I

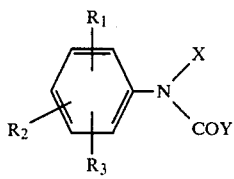

wherein
$R_1$, $R_2$, independently, are H or $CH_3$
$R_3$ is H, Cl, Br,
X is $CH(CH_3)COOCH_3$, 2-oxo-tetrahydrofuran-3-yl, 2-oxo-tetrahydrothien-3-yl or 2-oxo-1,3-oxazolidin-3-yl and
Y is $CH_2OCH_3$, 2-furyl, benzyl, $CH_2Cl$, cyclopropyl or 3-isoxazolyl,
in association with
(b) anilazine of formula II

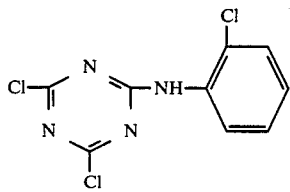

is particularly effective in combatting or preventing fungal diseases.

Anilazine is the common name for 2,4-dichloro-6-(2-chloroanilino)-1,3,5-triazine, which compound is known to be a protective fungicide effective against pathogens including Botrytis, Septoria, Plasmopara, Pseudocercosporella and Colletotrichum spp. (compare for example, U.S. Pat. No. 2,720,480).

Preferred compounds of formula I have one or more of the following features:
At least one of $R_1$, $R_2$, $R_3$ is different from H;
$R_3$ is hydrogen, 3-Cl or 3-Br;
$R_1$ and $R_2$ are $CH_3$ in the 2,6-position and $R_3$ is H, 3-Cl or 3-Br;
$R_1$ and $R_2$ are H and $R_3$ is 3-Cl;
X is $CH(CH_3)COOCH_3$, 2-oxo-tetrahydrofuran-3-yl or 2-oxo-1,3-oxazolidin-3-yl.

Examples of valuable oomycetes controlling fungicidal compounds of formula I are those wherein X, Y, $R_1$, $R_2$ and $R_3$ are
(i) $CH(CH_3)COOCH_3$, 2-furyl, 2-$CH_3$, 6-$CH_3$ and H resp. (common name furalaxyl)
(ii) $CH(CH_3)COOCH_3$, $CH_2$—$OCH_3$, 2-$CH_3$, 6-$CH_3$ and H resp. (common name metalaxyl)
(iii) $CH(CH_3)COOCH_3$, benzyl, 2-$CH_3$, 6-$CH_3$ and H resp. (common name benalaxyl)
(iv) 2-oxo-tetrahydrofuran-3-yl, $CH_2Cl$, 2-$CH_3$, 6-$CH_3$ and H (common name milfuram)
(v) 2-oxo-1,3-oxazolidin-3-yl, $CH_2$—$OCH_3$, 2-$CH_3$, 6-$CH_3$ and H resp. (common name oxadixyl)
(vi) 2-oxo-1,3-oxazolidin-3-yl, $CH_2$—$OCH_3$, 2-$CH_3$, 6-$CH_3$, 3-Cl resp.
(vii) 2-oxo-1,3-oxazolidin-3-yl, $CH_2$—$OCH_3$, 2-$CH_3$, 6-$CH_3$, 3-Br resp.
(viii) 2-oxo-tetrahydrofuran-3-yl, cyclopropyl, 3-Cl, H and H resp. (common name cyprofuram)
(ix) 2-oxo-tetrahydrofuran-3-yl, $CH_2OCH_3$, 2-$CH_3$, 6-$CH_3$ and H resp.
(x) $CH(CH_3)COOCH_3$, 3-isoxazolyl, 2-$CH_3$, 6-$CH_3$ and H resp.

Compounds of formula I are known or may be obtained according to known processes. (compare for example, DE-OS No. 3,229,000).

It has been found, that the use of Anilazine of formula II in combination with a compound of formula I, particularly with one of the compounds (i) to (x) indicated above, more particularly with furalaxyl (i), metalaxyl (ii), benalaxyl (iii), milfuram (iv) or oxadixyl (v), preferably with metalaxyl (ii) or oxadixyl (v), especially with the latter, surprisingly and substantially enhances the effectiveness of the latter against such fungi, and vice versa. Additionally, the method of the invention is effective against a wider spectrum of fungi than that, that can be combatted with the active ingredients of this method when used solely.

Accordingly, the invention provides an improved method of combatting fungi. Suitable examples of fungi that can be advantageously combatted by the method of the invention include fungi of the class Oomycetes such as Phytophthora spp., Plasmopara spp., Peronospora spp., Pseudo-peronospora spp., Sclerophthora spp., Bremia spp. and Pythium spp. and of the class of the Deuteromycetes such as Alternaria spp. Crops in which the method of the invention may be used include by way of example grapevines, tomato, hops, cacao, tobacco, potato, lettuce and eucalyptus.

The method of the invention comprises applying to the locus, in admixture or separately, a fungicidally effective aggregate amount of a compound of formula I and Anilazine of formula II.

The term crop as used herein is intended to embrace cultivated plants and any other desired plant growth.

Preferably the compounds of formula I are applied at a rate of 100–400 g/ha, particularly 150–300 g/ha, e.g. 200 g/ha in association with 200–2000 g/ha, particularly 1000 to 1600 g/ha, e.g. 1400 g/ha, of Anilazine of formula II. The method of the invention is i.a. a useful alternative in cases were the combined treatment of a compound of formula I with a dithiocarbamate (such as mancozeb, maneb, propineb, zineb) is not desirable, particularly where the fungi are Phytophthora spp. or related species. The method shows also a surprisingly good efficacy against Alternaria spp. such as *Alternaria solani* in potato.

Other pesticides e.g. fungicides, bactericides, insecticides, acaricides, herbicides or plant growth regulating agents may be used in addition to the above associated active ingredients, to enhance the activity of the association of the invention or to widen its spectrum of activity. So it may be advantageous to use an additional contact fungicide in the method of the invention.

Examples of contact fungicides suitable for use in combination with the method of the invention are one or more fungicides selected from a copper fungicide (e.g. cuprous oxide, copper (II) oxychloride, cupric hydroxide, copper (II) calcium sulphate, copper (II) calcium oxychloride, Bordeaux mixture or Burgundy mixture); captan (N-trichloromethylthio)-4-cyclohexene-1,2-dicarboximide); folpet (N-trichloromethylthio)-phthalimide); dichlofluanid (N-dichlorofluoromethylthio)-N',N'-dimethyl-N-phenylsulfamide); dithianon (2,3-dicyano-1,4-dithia-anthraquinone) and dithiocarbamates such as mancozeb (manganese zinc ethylene bisdithiocarbamate), maneb (manganese ethylene bisdithiocarbamate), propineb (zinc-(N,N'-propylene-1,2-bisdithiocarbamate)) and zineb (zinc ethyl bisdithiocarbamate). Such additional contact fungicide(s) may in general be applied at a rate of 200–2000 g/ha.

Other additional fungicides which may advantageously be used in the method of the invention are cymoxanil (2-cyano-N(ethylaminocarbonyl)-2-methoximino acetamide) and phosetyl-Al (aluminium tris-(O-ethylphosphonate)), particularly cymoxanil.

A preferred method of the invention comprises combatting fungi with a fungicidally effective aggregate amount of a compound of formula I, anilazine of formula II and cymoxanil or phosetyl-Al.

Cymoxanil is conveniently used at a rate of 40–160 g/ha, particularly 60–120 g/ha, e.g. 80 g/ha in such method: for phosetyl-Al the amount to be applied in such method of the invention is conveniently 750–2500 g/ha, particularly 1000–2000 g/ha, e.g. 1500 g/ha.

The invention also provides fungicidal compositions comprising a compound of formula I and Anilazine of formula II.

Such compositions may additionally contain further active agents, e.g. fungicides, such as contact fungicides, for example, the contact fungicides mentioned hereinabove, or cymoxanil, or phosetyl-Al.

In the compositions of the invention the weight ratio compound of formula I: Anilazine lies preferably in the range of 1:2 to 1:16, more preferably of 1:4 to 1:8, for example at 1:5.

Where the compositions of the invention comprise additionally a further contact fungicide, the weight ratio compound of formula I: contact fungicide lies preferably in the range of 1:2 to 1:10, and where Folpet, Captan, Mancozeb, Maneb or Propineb are used, more preferably 1:4 to 1:9, particularly 1:5 to 1:8 e.g. 1:7.

Where the compositions of the invention comprise additionally cymoxanil, the weight ratio of a compound of formula I: cymoxanil is conveniently from 10:1 to 1:3, preferably from 1:0.3 to 1:3.

Where the compositions of the invention comprise additionally phosetyl-Al, the weight of a compound of formula I: phosetyl-Al is conveniently in the range of 1:15 to 1:3, particularly 1:10 to 1:5 e.g. 1:7.

The composition of the invention may be employed in any conventional form, for example in the form of a twin pack, an instant granulate, a flowable or a wettable powder in combination with agriculturally acceptable adjuvants. Such compositions may be produced in conventional manner, e.g. by mixing the active ingredients with appropriate adjuvants (diluents and optionally other formulating ingredients such as surfactants).

The term diluent as used herein means any liquid or solid agriculturally acceptable material—including carriers—which may be added to the active constituents to bring them in an easier or improved applicable form, respectively, to a usable or desirable strength of activity. It can for example be talc, kaolin, diatomaceous earth, xylene, or water.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% agriculturally acceptable surfactant and 10 to 99.99% solid or liquid adjuvant(s), the active agent consisting of at least one compound of formula I together with Anilazine of formula II, and optionally other active agents, particularly phosetyl-Al or cymoxanil, preferably the latter. Concentrate forms of compositions generally contain in between about 2 and 80%, preferably between about 5 and 70% by weight of active agent. Application forms of formulation may for example contain from 0.01 to 20% by weight, preferably from 0.01 to 5% by weight of active agent.

The invention is illustrated by the following Example wherein parts and percentages are by weight and temperatures are in °C.

TEST: Synergistic Activity

Young tomato plants are sprayed with an aqueous spray liquid containing either a compound of formula I or Anilazine of formula II alone or in association according to the invention. Each component and the combination are applied in 4 to 5 concentrations between 0.0125 to 0.00002% until the run-off. The combination is tested in various weight ratios.

Two hours later, the treated plants are inoculated with a spore suspension of *Phytophthora infestans* and the plants are then transferred to a tent providing 100% relative atmospheric humidity at an ambient temperature of 16° C. and a day length of 16 hours. Disease control is evaluated 4–5 days later by comparing the treated plants with untreated, similarly inoculated plants.

The results are plotted in a dose-response curve according to the logit-log (or probit-log) system as described by D. L. Finney in Probit Analysis (1971, 3. Ed. Cambridge University Press).

These dose-response curves are used to establish the EC 90 of the combinations in a weight compound of formula I: Anilazine of 1:2, 1:4, 1:8 and 1:16. (EC 90 is the concentration allowing 90% control of fungal infestation). The thus experimentally found values [EC 90 (exp.)] are compared with the values that would have been found were only a complementary of the components present [EC 90 (theor.)]. The EC 90 (theor.) is calculated according to Wadley. The ratio EC 90 (theor.): EC 90 (exp.) expresses the factor of synergism (SF; in the case of synergism, SF > 1).

Similar tests are also run using tomato plants infested with *Alternaria solani*.

The results obtained when using Oxadixyl (Iv) as compound of formula I are expressed in the following Table I.

TABLE I

| Compounds | Tomato/Phytophthora EC 90 (mg/l) | | | Tomato/Alternaria EC 90 (mg/l) | | |
|---|---|---|---|---|---|---|
| | theor. | exp. | SF | theor. | exp. | SF |
| Oxadixyl (Iv) | | 24 | | | 10000 | |
| Anilazine (II) | | 424 | | | 1495 | |
| Iv:II = 1:2 | 65 | 28 | 2.3 | 2226 | 401 | 5.6 |
| Iv:II = 1:4 | 98 | 32 | 3.1 | 1862 | 317 | 5.9 |
| Iv:II = 1:8 | 149 | 35 | 4.2 | 1679 | 640 | 2.6 |

FORMULATION EXAMPLE

Wettable Powder

A mixture of
50% Anilazine (100%)
10% Oxadixyl (100%)
1% Sodium alkylnaphthalenesulfonate
5% Sodium alkylarylsulfonate-Formaldehyde condensate
5% highly disperse silica and
29% kaolin
is ground until the particles have the desired size: A 60% wettable powder containing 50% of anilazine and 10% of oxadixyl is obtained.

What we claim is:

1. A method of combatting fungi in a locus, which comprises applying to the locus
(a) the compound of the formula

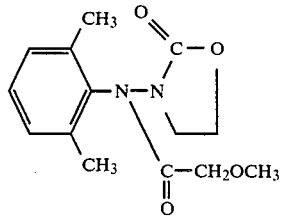

in association with
(b) the compound of the formula

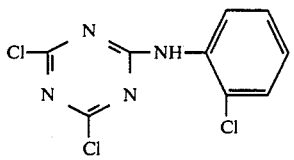

in admixture or separately in a fungicidally effective aggregate amount, said (a) and (b) being applied in a weight ratio of said (a) to (b) in the range of from 1:2 to 1:8.

2. The method of claim 1 in which the weight ratio of (a) to (b) is in the range of from 1:4 to 1:8.

3. The method of claim 2 in which component (a) is applied at a rate of from 150 to 300 grams/hectare and component (b) is applied, at a rate of from 1000 to 1600 grams per hectare.

4. The method of claim 1 in which component (a) is applied at a rate of from 100 to 400 grams/hectare and component (b) is applied at a rate of from 200 to 2000 grams/hectare.

5. A fungicidal composition comprising an Oomycetes controlling effective amount of: a component (a) which is the compound of the formula

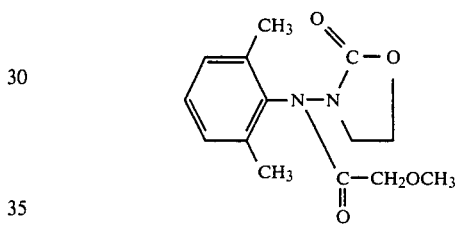

and a component (b) which is the compound of the formula

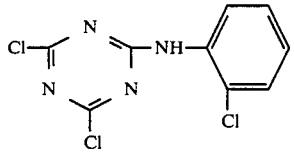

the weight ratio of component (a) to component (b) in said composition being in the range of from 1:2 to 1:8.

6. A composition of claim 5 in which the weight ratio of component (a) to component (b) is in the range of from 1:4 to 1:8.

* * * * *